US005697962A

United States Patent [19]
Brink et al.

[11] Patent Number: 5,697,962
[45] Date of Patent: Dec. 16, 1997

[54] THERAPEUTIC WRAP

[75] Inventors: N. Keith Brink; Dan H. Gibson, both of Oklahoma City, Okla.

[73] Assignee: Dura-Kold Corporation, Oklahoma City, Okla.

[21] Appl. No.: 537,347

[22] Filed: Sep. 29, 1995

[51] Int. Cl.$^6$ ................................................ A61F 7/00
[52] U.S. Cl. .......................... 607/108; 607/112; 607/114; 126/204
[58] Field of Search .................. 607/96, 108–112, 607/114; 224/222, 236, 660–665; 126/204

[56] References Cited

U.S. PATENT DOCUMENTS

| | | | |
|---|---|---|---|
| 1,473,506 | 11/1923 | Nessler . | |
| 1,567,931 | 12/1925 | Epler . | |
| 1,927,751 | 9/1933 | Mensi | 128/258 |
| 1,964,962 | 7/1934 | Rosenblum | 128/268 |
| 2,547,886 | 4/1951 | Poux | 62/1 |
| 2,602,302 | 7/1952 | Poux | 62/1 |
| 2,769,308 | 11/1956 | Krasno | 62/1 |
| 2,800,456 | 7/1957 | Shepherd | 252/70 |
| 2,984,231 | 5/1961 | Conrad et al. | 2/7 |
| 3,149,943 | 9/1964 | Amador | 62/4 |
| 3,429,138 | 2/1969 | Goldmerstein | 62/259 |
| 3,463,161 | 8/1969 | Andrassy | 128/402 |
| 3,491,761 | 1/1970 | Baker | 128/402 |
| 3,500,014 | 3/1970 | Longo | 219/211 |
| 3,506,013 | 4/1970 | Zdenek | 128/402 |
| 3,802,215 | 4/1974 | Rowe | 62/259 |
| 3,871,376 | 3/1975 | Kozak | 128/275.1 |
| 3,889,684 | 6/1975 | Lebold | 128/402 |
| 3,900,035 | 8/1975 | Welch et al. | 128/402 |
| 3,913,559 | 10/1975 | Dandliker | 126/263 |
| 3,950,789 | 4/1976 | Konz et al. | 2/93 |
| 4,055,188 | 10/1977 | Pelton | 128/402 |
| 4,081,150 | 3/1978 | Tyson | 128/402 |
| 4,204,543 | 5/1980 | Henderson | 128/402 |
| 4,324,111 | 4/1982 | Edwards | 62/457 |
| 4,326,533 | 4/1982 | Henderson | 128/402 |
| 4,381,025 | 4/1983 | Schooley | 150/2.4 |
| 4,404,820 | 9/1983 | Romaine | 62/530 |
| 4,513,053 | 4/1985 | Chen et al. | 428/221 |
| 4,527,566 | 7/1985 | Abare | 128/402 |
| 4,556,055 | 12/1985 | Bonner, Jr. | 128/82.1 |
| 4,576,169 | 3/1986 | Williams | 128/402 |
| 4,619,678 | 10/1986 | Rubin | 62/4 |
| 4,625,729 | 12/1986 | Roney | 128/402 |
| 4,628,932 | 12/1986 | Tampa | 128/402 |
| 4,676,247 | 6/1987 | Van Cleve | 607/112 |
| 4,700,706 | 10/1987 | Münch | 128/403 |
| 4,832,030 | 5/1989 | DeCanto | 128/380 |
| 4,931,333 | 6/1990 | Henry | 428/76 |
| 4,981,135 | 1/1991 | Hardy | 128/402 |
| 5,005,374 | 4/1991 | Spitlar | 62/259.3 |
| 5,016,629 | 5/1991 | Kanare | 607/114 |
| 5,069,208 | 12/1991 | Noppel et al. | 128/403 |
| 5,353,975 | 10/1994 | Libertucci | 224/662 |
| 5,391,198 | 2/1995 | Cheney, III et al. | 607/114 |
| 5,395,399 | 3/1995 | Rosenwald | 607/114 |
| 5,484,448 | 1/1996 | Steele et al. | 607/114 |
| 5,496,358 | 3/1996 | Rosenwald | 607/108 |
| 5,507,793 | 4/1996 | Hodges | 607/109 |

FOREIGN PATENT DOCUMENTS 1185811  3/1970  United Kingdom .

OTHER PUBLICATIONS

Photographs #1–#5.
Dura*Kold Corporation brochure entitled "Re–usable Ice Wrap".
Dura*Kold Corporation brochure entitled "Re–usable Compression Ice Wraps".

(List continued on next page.)

*Primary Examiner*—Robert L. Nasses, Jr.
*Attorney, Agent, or Firm*—Dougherty & Hessin, P.C.

[57] ABSTRACT

A therapeutic wrap that can be releasably connected to a body has one or more chambers for holding one or more discrete hot or cold members. Openings into the chambers and connectors for holding the wrap to the body are provided so that the hot or cold member(s) can be accessed in the chamber(s) without substantially moving the wrap relative to the body to which it is connected.

5 Claims, 2 Drawing Sheets

OTHER PUBLICATIONS

Dura*Kold Corporation brochure entitled "Equine, Re-usable Compression Ice Wraps".

Elasto-Gel brand Cervical Collar advertisement entitled "Elasto-Gel Cervical Collar provides soothing relief for all your pains in the neck!"; Elasto-Gel brand Sinus Mask advertisement entitled Say good-bye to those excruciating sinus-triggered migraines!

ErgoMed Inc. advertisement entitled "Only ErgoForm™ contoured cold packs fit the treatment to the trauma".

Icewrap™ brand advertisement entitled "Don't Miss Your Next Workout", from Promises Kept (Summer 1992).

Quinta -Group Limited brochure entitled "Mild Pack™ Micro-Crystalline Ice For Long Duration".

Physicians & Nurses Manufacturing Corporation brochure entitled "Cold Relief Pack".

Thera•P brand brochure entitled "Say goodbye to melting ice and dripping towels!".

Spenco® brand advertisement entitled "Spenco® Thermawrap™ Compress".

SmartPractice advertisement entitled "ThermoCare™ The All-In-One Hot and Cold Pack".

EBI® Medical Systems advertisement entitled "EBI® Temptek™ vs. Ice: Compare the Cold, Hard Facts", from Orthopaedic Review.

Breg® brochure entitled "Polar Care®Cold Therapy".

Cryo/Cuff® brand brochure entitled "Cryo/Cuff® compression dressings".

Guardian Products Inc. brochure entitled "I.C.E. DOWN® A Refreezable Flexible Cold Therapy Wrap".

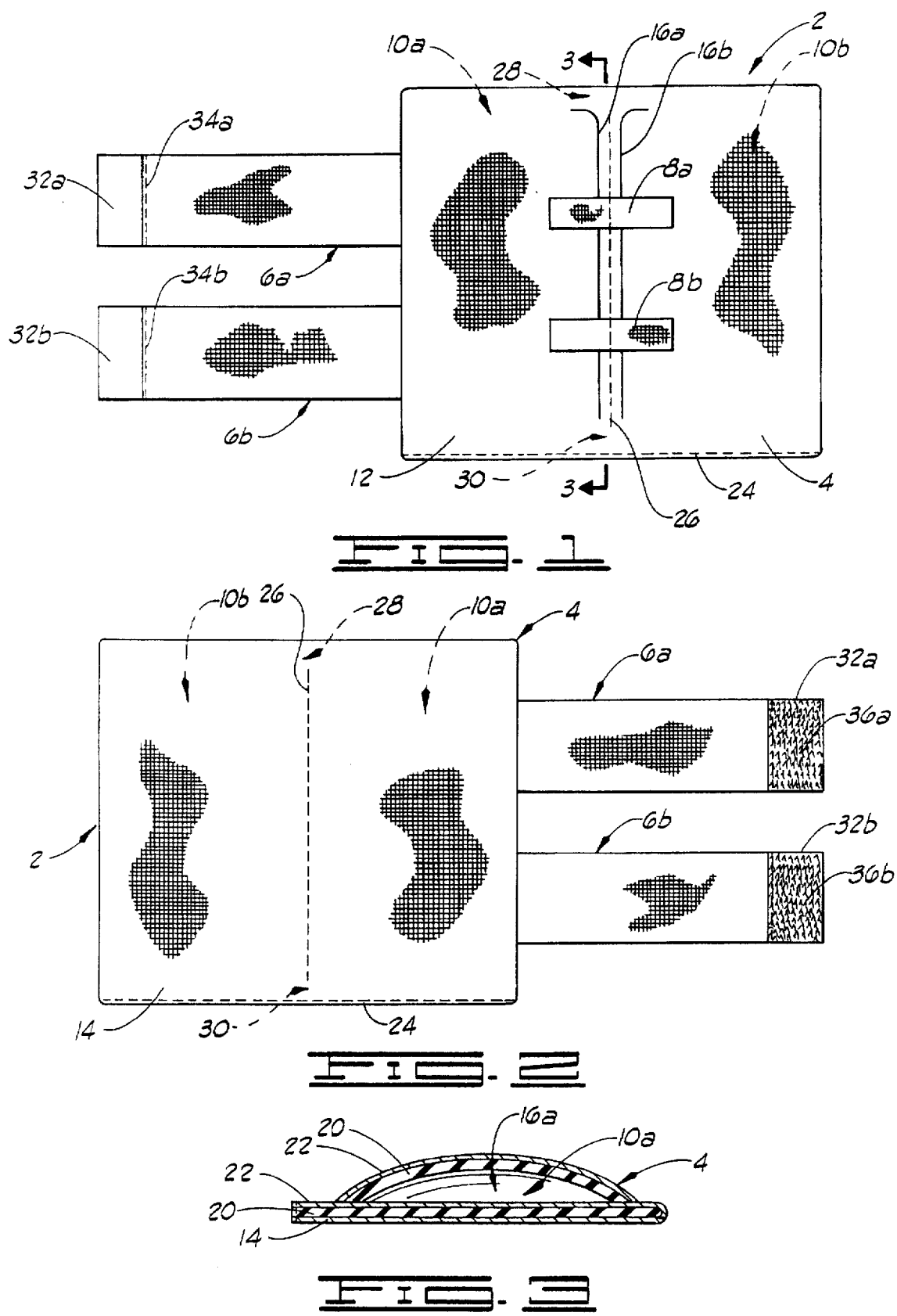

THERAPEUTIC WRAP

BACKGROUND OF THE INVENTION

This invention relates generally to therapeutic wraps providing heat or cold to a body portion. In a particular implementation and use, the wrap has two chambers that are to be disposed on opposite sides of a knee and that receive hot or cold substances without being removed from the knee.

Many injuries to humans and animals are treated with heat or cold. For example, cryotherapy is used to treat soft tissue trauma such as from sports injuries and surgeries.

When heat or cold is to be applied for an extended period of time, the hot or cold substance typically needs to be replaced. For example, with a conventional ice bag, the ice melts and needs to be replaced if cooling is to be maintained. Likewise, a hot water bottle needs to be refilled with hot water after a period of time.

Even more recent types of therapeutic wraps that provide heating or cooling in an improved manner of retaining the hot or cold substance and of securing it to the body portion, must have their temperature control agent replaced from time to time. With regard to current foam, elastic or nylon wraps designed to wrap around various body parts and to secure thereto with elastic straps and hook-and-pile fasteners, interior compartments must be accessed to retrieve and replace the hot or cold members contained within the compartments. To accomplish this, the wraps must be partially disconnected or completely removed whereby the wrap is displaced relative to the body portion undergoing treatment. This is inconvenient for the user, particularly if the wraps are applied over surgical dressings or underneath braces or orthotic supports. Because braces and orthotic supports are held in place by straps, etc., they too have to be partially undone or completely removed to get to the underneath wrap. This can also be uncomfortable, painful or damaging to the patient. For example, edema may occur at the site of the injury, and this condition causes pain and makes the patient uncomfortable when the affected area has to be moved to replace a therapeutic wrap.

Systems that circulate liquid through a wrap are one attempt at providing hot or cold therapy without having to move the wrap by which the temperature agent is applied to the body part. In such a system, a wrap having a fluid circuit is secured to the body part and a heated or cooled liquid is circulated from a pump or gravity-feed device. This does not require any disconnection or displacement of the wrap to maintain the desired temperature agent in the wrap since the agent is continuously provided from the external source. This type of system is, however, significantly more expensive than a self-contained wrap. It is also less convenient should the patient need to be moved from one location to another.

Because of the desire to prevent any unnecessary movement at an injury site on a human or animal and of the shortcomings of conventional therapeutic wraps and fluid flow systems referred to above, there is the need for an improved therapeutic wrap. Specifically, there is the need for such a wrap that does not have external components such as fluid lines and yet does enable an internally carried hot or cold member to be replaced without disconnecting or significantly moving the wrap relative to the body part to which the wrap is connected.

SUMMARY OF THE INVENTION

The present invention overcomes the above-noted and other shortcomings of the prior art by providing a novel and improved therapeutic wrap. The wrap of the present invention permits access to one or more inside storage chambers or pockets through the outer shell or casing of the wrap without disconnecting the wrap or significantly moving it relative to a body portion when the wrap is in use. Openings in the outside surface of the wrap allow hot or cold members to be inserted and removed without having to remove or partially undo the wrap or to unhook or unbuckle any strapping mechanism when it is time to remove or replace the inside hot or cold member.

The invention has a simple construction which has no connections to external heating or cooling equipment and which also allows the caregiver or patient to use the invention with little or no movement, creating little or no pain or discomfort. Many chronic ailments may also be treated by using this invention. Ease of use converts into patient compliance thus creating a product friendly for its users.

The present invention provides an apparatus for applying heat or cold to a body. The apparatus comprises a container adapted to be releasably connected to the body along a direction of wrap about a portion of the body. The container has a chamber defined therein for holding a discrete temperature mass that provides the heat or cold. The container further has an elongated portal defined therein transverse to the direction of wrap so that the portal does not substantially curve along the direction of wrap whereby the chamber is accessible through the portal to insert or remove the temperature mass without disconnecting the container from the body.

Stated another way, the apparatus comprises connector means for releasably connecting the apparatus adjacent a body to which heat or cold is to be applied. This connector means includes an elastic member having a plurality of hook elements connected thereto for releasably connecting to pile material. The apparatus further comprises container means, connected to the connector means, for receiving a temperature member providing the heat or cold. The container means includes a foam and pile side and a mesh side connected together to define a chamber. The foam and pile side has an opening into the chamber, which opening is defined through the foam and pile side such that the chamber is accessible to insert and extract the temperature member without releasing the connector means. The apparatus can further comprise a closure member having one end fixed to the foam and pile side to one side of the opening and having another end with hook members adapted to engage the pile of the foam and pile side on the other side of the opening to hold the opening in a closed position.

More specifically, the present invention provides a wrap for holding a hot or cold substance adjacent a body, comprising a pouch having at least two chambers for the hot or cold substance, which pouch is adapted to be conformed to a portion of the body where heat or cold from the hot or cold substance is to be applied on opposite sides of a fold line defined between at least two of the chambers. The wrap further comprises a strap connected to the pouch and adapted to secure the pouch to the body without impeding ingress and egress into or out of any of the chambers of the pouch for inserting or removing the hot or cold substance. In a particular implementation, the wrap is adapted for a human knee so that the fold line overlies the patella of the knee and the chambers are disposed on opposite sides thereof in response to applying the wrap to the knee. Openings through the outer surface of the pouch into the chambers provide access without significantly moving the wrap relative to the knee.

Therefore, from the foregoing, it is a general object of the present invention to provide a novel and improved therapeutic wrap. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 1 a side view of one embodiment of a therapeutic wrap of the prevent invention.

FIG. 2 is a side view of the therapeutic wrap opposite the view shown in FIG. 1.

FIG. 3 is a sectional view taken along line 3—3 shown in FIG. 1, but showing the respective slit in an open position.

DETAILED DESCRIPTION OF PREFERRED EMBODIMENTS

Figure 4:
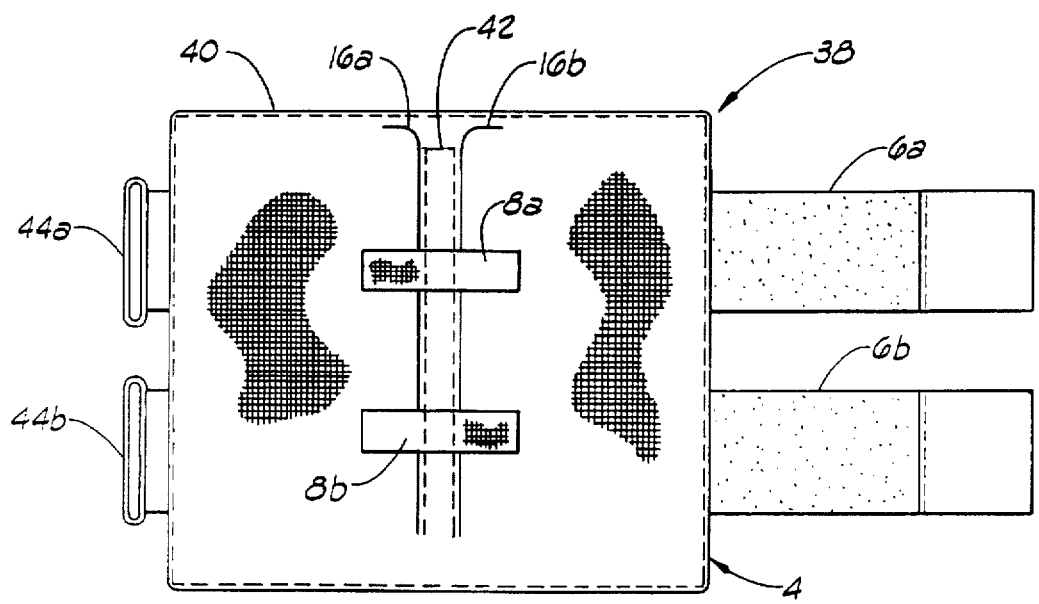
FIG. 4 is a side view of another embodiment of a therapeutic wrap of the present invention.

The present invention provides an apparatus for applying heat or cold to a body. One preferred embodiment of this apparatus is shown in FIGS. 1–3. The apparatus of this preferred embodiment, identified by the reference numeral 2, is specifically a therapeutic wrap that can be secured to a body part of a human or animal. A particular implementation of the embodiment of FIGS. 1–3 is used as a knee wrap.

The apparatus 2 includes a container 4, straps 6a, 6b, and means for maintaining openings into chambers in the container 4 in closed positions. In FIGS. 1–3, this means is embodied by two pairs of butterfly straps 8a, 8b. Each of these components will be more fully described in the following paragraphs.

The container 4 is constructed so that it can receive a discrete temperature member providing heat or cold to an adjacent body portion and so that it can conform to the body portion when the apparatus 2 is connected thereto. The temperature member itself does not form a part of the present invention but can be implemented by any suitable means providing either heat or cold as desired. For example, ice cubes or artificial ice products can provide the temperature member when cold is desired. A gel pouch is another non-limiting example. When cold is desired, a preferred implementation is the mat-type cold pack member used in products sold by Dura-Kold Corporation in Oklahoma City, Oklahoma; however, the apparatus 2 is preferably adapted so that it can receive various types of heating or cooling products, thereby providing the apparatus 2 with a versatility in that it is not limited to use with a single type of heating or cooling product. This versatility does not, however, include use of the apparatus 2 as a direct part of the flow type system described above. That is, the therapeutic wrap of the present invention is not connected to any external temperature source, but rather wholly contains the temperature source(s) within itself.

The container 2 is specifically implemented as a flexible pouch having at least one chamber defined therein. In the apparatus 2, two chambers 10a, 10b are defined. These are defined between sides 12 (FIG. 1) and 14 (FIG. 2) of the container 4. The side 12 has openings into each of the chambers; and the side 14 is to be disposed adjacent, or facing, the portion of the body where heat or cold is to be applied.

The openings into the chambers are defined by respective slits 16a, 16b, formed, such as by cutting, through the side 12 of the container 4. The slits 16a, 16b are transverse to the wrapping direction of the container 4 (which is also transverse to the length of the rectangular pouch specifically illustrated in FIGS. 1–3). Preferably, the slits are perpendicular or at least substantially transverse to the direction of wrap so that the slits do not substantially curve along the direction of wrap, thereby facilitating access into the chamber with the respective slit to insert or remove the temperature mass without disconnecting the container 4 from the body. In the illustrated embodiment, the slits 16 are parallel to each other and spaced near each other at the middle of the wrapping direction dimension of the container 4.

Each slit 16a, 16b defines an elongated portal through which ingress and egress into and out of the respective chamber is permitted. The remaining perimeters of the respective chambers are closed to outside access. Thus, in the preferred embodiment of FIGS. 1–3 the temperature means can be inserted and extracted relative to a chamber only through the respective slit.

It is important that the slit is sufficiently transverse to the wrap direction of the container 4 because this enables easy access through the slits into the respective chambers to insert or remove a respective temperature mass without disconnecting the container from the body once it is connected to the body. That is, if the slits were parallel to the wrap direction, the wrap could not be curved to conform to the body if the temperature element were elongated and rigid (e.g., due to being frozen). Even if the temperature element could be conformed, such as by being curved around a knee, it would be difficult to readily remove such a conformed element due to binding that could occur between the curved container and the curved temperature element.

Figure 5:
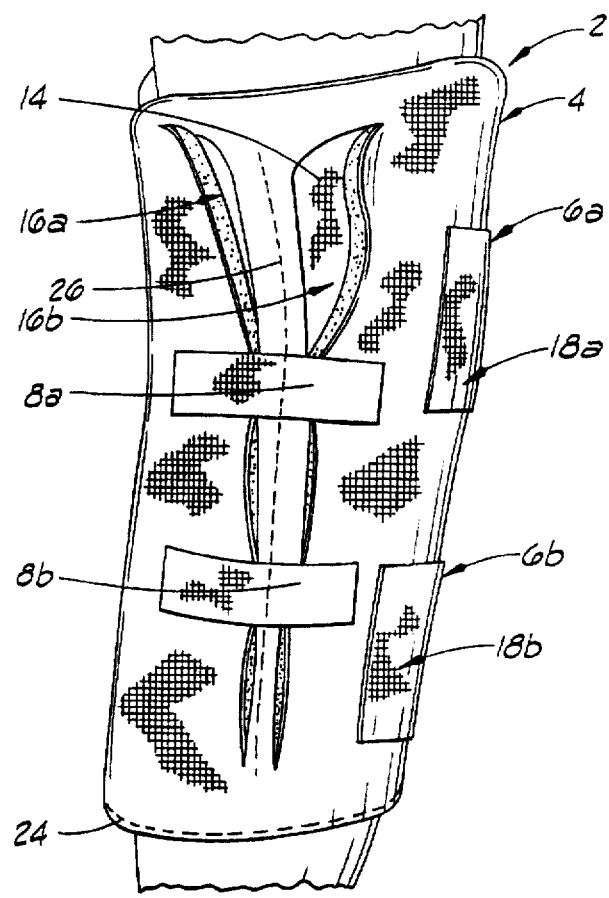
FIG. 5 is a view showing the therapeutic wrap of FIG. 1 attached at the knee of a human.

The container 4 is connected to the body by means of the straps 6a, 6b. Each of the straps 6 has a fixed end connected to a respective edge of the pouch. Each strap 6 also has a free end adapted to connect to the pouch so that the respective strap secures the pouch to the body without obstructing access through the slit 16 and without obstructing operation of the slit or chamber closure straps 8a, 8b. FIG. 5 illustrates this as it shows the apparatus 4 secured to the knee of a user with connected free ends 18a, 18b of the straps 6a, 6b spaced from the slit closure tabs 8a, 8b. Thus, each strap 6 has one end fixed to one side of the openings defined by the slits 16 and another end adapted to releasably connect to the pouch on another side of the openings after the free end is extended around the portion of the body where the apparatus 2 is to be mounted. In this manner the straps define connector means which connects around a portion of the body opposite the openings defined by the slits 16 and which attaches to the container 4 on opposite sides of the openings. Other releasable connector means embodiments can, of course, be used whether they are of a strap or non-strap type (e.g., another strap type connector is to have the straps 6a, 6b formed as integral parts of and of the same material as side 12).

The materials and construction of a particular implementation of the apparatus 2 will next be described; however, it is noted that these details are not limiting of broader aspects of the invention as other types of materials and methods of construction can be used.

The side 12 of the container 4, which with side 14 define a flat pouch in the laid out views of FIGS. 1 and 2, is made of a hook-sensitive outer layer laminated to a foam substrate for comfort, product stability and insulation to direct the hot or cold therapy toward the affected area. A particular type of material used is the foam and pile material used in prior therapeutic wrap products from Dura-Kold Corporation. Referring to FIG. 3, the foam substrate is identified by the reference numeral 20 and the pile surface layer is identified by the reference numeral 22.

The side 14 of the apparatus 2 is made of a lightweight mesh that offers a temperature barrier but also is porous enough to allow the temperature flow that is needed to provide the desired treatment. The mesh side 14 forms a layer between the foam substrate and the skin of the patient to which the apparatus 2 is connected. Examples of this material include nylon, acetate, polyester or any other suitable material with porous qualities. The selected material preferably is of a type that wicks away any condensation that may occur.

At least when a self-contained temperature member (e.g., the above-mentioned mat-type cold pack product) is used with the wrap, the materials of sides 12 and 14 need not define the container 4 as being watertight or waterproof, which it clearly will not be if open-pore mesh material is used as referred to above.

The material of side 12 and the material of side 14 are joined by inside stitching along three sides with outside stitching on the fourth side as shown in FIGS. 1 and 2. For example, three sides can be externally stitched and the sides turned outside in and then closed by outside stitching 24 on the fourth side as illustrated in FIGS. 1 and 2. Other means for attaching the sides can be used. Non-limiting examples include heat or fusion processes.

Outside stitching 26 across the middle of the container 4 divides the two adjacent chambers 10a, 10b which communicate via channels 28, 30 formed by ending the central stitching 26 short of each lengthwise edge. This stitching 26 also holds the butterfly slit closure straps 8a, 8b as shown in FIG. 1.

The wrap securing straps 6 of the illustrated embodiment are made of an elastic material to which hook containing pads 32a, 32b are attached at free ends 18a, 18b, respectively, by sewing with the stitching 34a, 34b as illustrated in FIG. 1. The hook elements 36a, 36b of the pads releasably connect to the pile surface of the material layer 22 referred to above. The elastic of the straps 6 allows the product to be used around different sizes of body portions and minimizes any tourniquet effect; however, elasticity is not required or a limitation of the invention (e.g., if the straps are implemented as integral with and made of the foam and pile material of side 12, there would not be substantial elasticity in such straps). The fixed ends of the straps 6 are sewn along one widthwise edge of the container 4 as shown in the drawings. The straps 6 are parallel to each other and extend in the direction of wrap in the illustrated embodiments. This is also along the length direction for the illustrated rectangular embodiments having lengths in the wrap direction greater than the widths of the containers.

The chamber closure straps 8 have quick release hook material which engages the pile material of the surface 12 to close the openings into the chambers so that the hot or cold elements are retained inside the chambers.

The materials of construction are preferably of light weight so that the overall weight of the apparatus is insignificant to the user.

Another embodiment of the present invention is shown in FIG. 4. This embodiment, generally identified by the reference numeral 38, is also particularly adapted for use with a knee. It has the same components as the previously described embodiment as indicated by the same reference numerals except external stitching 40 is used around the entire perimeter and a double stitch 42 is disposed between the two slits to define the two chambers of the container 4.

A more significant distinction is that the embodiment of FIG. 4 includes plastic (or other suitable material) loops 44a, 44b sewn in to guide the straps 6 to the proper areas of the body portion to which the apparatus 2 is to be connected. Each loop 44 in this embodiment is sewn on the same widthwise end of the container 4 opposite the end or edge to which the straps 6 are fixed. When the wrap 38 is used, the straps 6 preferably extend behind the body portion and then through the respective loop 44, at which point the strap 6 is doubled back over itself and attached to the strap itself which in at least this embodiment is preferably made of an elastic pile material suitable for receiving the hook elements at the end of the respective strap 6.

Referring to FIG. 5, it will be readily apparent how the present invention facilitates the insertion and removal of one or more temperature members into or out of the respective chambers 10 without disconnecting the apparatus 2 (or 38) or significantly moving it relative to the knee illustrated as the body portion to which the apparatus 2 is connected in FIG. 5. Once the apparatus 2 is secured to the body portion by (1) laying the container 4 at the place of application, (2) extending the straps 6 around the body part to the opposite side and (3) attaching the hook material of the straps 6 to the pile material of the container 4, the chambers 10a, 10b can still be readily accessed. The chambers 10 lie on opposite sides of a fold line defined between the slits 16a, 16b substantially in conjunction with stitch line 26. This fold line overlies the knee's patella and the chambers 10 thus overlie opposite sides of the knee joint where the heat or cold is to be applied. Access to the chambers 10 is accomplished by lifting the respective end tabs of the chamber closure straps 8 and peeling the surface 12 material back at the respective slit 16. One's hand can then be inserted into the chamber 10 to grasp the temperature element to pull it from the chamber. Insertion of the material is performed in a like manner. When the temperature element is in place in the chamber 10, the material of the side 12 is folded back down to close the slit 16 and the respective end tabs of the straps 8a, 8b are pressed down to secure to the pile material of the side 12.

From FIG. 5 it will be noted that it is important for the slits to run substantially parallel to the length of the limb to which the apparatus 2 is attached. If the slits were formed along the direction of wrap around the knee, the slits would curve around the circumference of the limb so that it would be difficult to insert or extract the temperature element without removing or otherwise loosening the apparatus 2.

Although the knee is used to illustrate one use of the present invention, the invention is not limited to only knees or other joints. It can be adapted to conform to any desired body portion, on human or animal, and still provide its many advantages. The size and shape of the apparatus of a particular implementation is selected to allow for proper fit around the desired areas of use. For instance, the embodiment of FIGS. 1-3 particularly adapted as a knee wrap allows for medial/lateral placement of the cold products in the chambers 10a, 10b with a safety gap between the cooling members to leave the patella uncovered.

Furthermore, the therapeutic nature of the invention is not solely with regard to trauma relief since it can also be used as a preventive item, such as after strenuous exercise or activity.

Additionally, an apparatus implementing the invention can be made sterile if need be. The product can be made totally disposable to eliminate any form of cross contamination. The product as particularly implemented above can be cleaned by washing in warm water and drying on low in an automatic dryer or by air drying.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. An apparatus for applying heat or cold to a knee, comprising a container for wrapping about a knee of a leg along a direction of wrap extending medially and laterally from a central fold line of said container, which central fold line is transverse to the direction of wrap and which central fold line is adapted to overlie the patella of the knee and extend parallel to the length of the leg when said container is wrapped about the knee, wherein said container has two vertically oriented chambers defined therein on opposite sides of, and parallel to, the central fold line such that one chamber adapted to overlie the medial side of the knee and extend along a portion of the length of the led from above to below the knee and the other chamber is adapted to overlie the lateral side of the knee and extend along a portion of the length of the led from above to below the knee when said container is wrapped about the knee, said chambers further adapted to hold respective discrete temperature masses to provide heat or cold to medial and lateral portions of the knee when said container is wrapped about the knee, and wherein said container further has two elongated vertically oriented portals defined therein transverse to said direction of wrap and parallel to the central fold line so that the portals do not substantially curve along said direction of wrap, wherein each said portal is adapted to open outwardly away from the knee when said container is wrapped about knee such that each said chamber is accessible through a respective one of said portals to insert or remove the respective temperature mass without removing said container from the knee and wherein said portals are on opposite sides of, but adjacent to, the central fold line of said container.

2. An apparatus as defined in claim 1, wherein said container includes:

a first side having a surface layer made of a pile material, wherein said first side has two cuts therethrough defining said two elongated portals, said two cuts spaced from each other such that a patella safety gap is defined therebetween whereby discrete temperature masses in said chambers will not overlie the patella of the knee;

a second side having a porous temperature barrier made of a mesh material, said second side connected to said first side around a periphery thereof; and stitching disposed across the middle of said first and second sides between said cuts to separate said two chambers, said stitching substantially conjunctional with the fold line of said apparatus, said stitching and fold line overlying the patella of the knee when said container is placed about the knee.

3. An apparatus as defined in claim 2, further comprising a strap to connect to said pile material so that said strap secures said apparatus to the knee without obstructing access through said cuts.

4. An apparatus as defined in claim 2, further comprising a portal closure strap connected to the outside of said first side of said container by said stitching, said portal closure strap including a hook material for engaging said pile material of said first side when at least one of said portals is in its closed position.

5. An apparatus as defined in claim 1, further comprising external closure means, connected to the outside of said container, for maintaining said portals in closed positions.

* * * * *

UNITED STATES PATENT AND TRADEMARK OFFICE
CERTIFICATE OF CORRECTION

Patent No.:     5,697,962

Dated:          December 16, 1997

Inventors:      N. Keith Brink and Dan H. Gibson

It is certified that errors appear in the above-identified patent and that said Letters Patent are hereby corrected as shown below:

Column 3, line 8, insert --is-- after "FIG. 1".

Column 3, line 67, delete "," after "16b".

Column 7, line 24, insert --is-- after "chamber".

Column 7, line 25, delete "led" and insert --leg--.

Column 7, line 28, delete "led" and insert --leg--.

Column 7, line 38, insert --the-- after "about".

Signed and Sealed this

Twenty-first Day of April, 1998

Attest:

BRUCE LEHMAN

Attesting Officer     Commissioner of Patents and Trademarks